United States Patent
Falkowski et al.

(10) Patent No.: US 11,964,927 B2
(45) Date of Patent: Apr. 23, 2024

(54) PRODUCTION OF ALKYLAROMATIC COMPOUNDS

(71) Applicant: ExxonMobil Chemical Patents Inc., Baytown, TX (US)

(72) Inventors: Joseph M. Falkowski, Hampton, NJ (US); Ivy D. Johnson, Lawrenceville, NJ (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 0 days.

(21) Appl. No.: 17/766,411

(22) PCT Filed: Sep. 30, 2020

(86) PCT No.: PCT/US2020/053510
§ 371 (c)(1),
(2) Date: Apr. 4, 2022

(87) PCT Pub. No.: WO2021/080754
PCT Pub. Date: Apr. 29, 2021

(65) Prior Publication Data
US 2024/0051898 A1 Feb. 15, 2024

Related U.S. Application Data

(60) Provisional application No. 62/926,174, filed on Oct. 25, 2019.

(30) Foreign Application Priority Data

Feb. 24, 2020 (EP) .................................... 20158965

(51) Int. Cl.
*C07C 2/66* (2006.01)
*B01D 15/08* (2006.01)
(Continued)

(52) U.S. Cl.
CPC ................ *C07C 2/66* (2013.01); *B01D 15/08* (2013.01); *B01J 8/0278* (2013.01); *B01J 20/226* (2013.01);
(Continued)

(58) Field of Classification Search
None
See application file for complete search history.

(56) References Cited

U.S. PATENT DOCUMENTS

| | | | |
|---|---|---|---|
| 3,293,192 A | 12/1966 | Maher et al. | .................. 252/430 |
| 3,308,069 A | 3/1967 | Wadlinger et al. | ........... 252/455 |

(Continued)

FOREIGN PATENT DOCUMENTS

| | | | | |
|---|---|---|---|---|
| EP | 0293032 | 5/1988 | ............. | C01B 35/10 |
| WO | WO1997/017290 | 5/1997 | ............. | C01B 33/38 |
| WO | WO2018/183012 | 10/2018 | ............. | B01J 29/00 |

OTHER PUBLICATIONS

Horcajada, P. et al. (2007) "Synthesis and Catalytic Properties of MIL-100(Fe), an iron(III) Carboxylate with Large Pores," *Chem. Comm.*, pp. 2820-2822.

(Continued)

*Primary Examiner* — Youngsul Jeong
*Assistant Examiner* — Alyssa L Cepluch

(57) ABSTRACT

A process for producing an alkylaromatic compound comprises providing a first feed comprising an alkylatable aromatic compound and a second feed comprising an alkylating agent, wherein at least the first feed contains an impurity compound comprising at least one of nitrogen, halogens, oxygen, sulfur, arsenic, selenium, tellurium, phosphorus, and Group 1 through Group 12 metals The first feed is passed through an adsorbent comprising a metal-organic framework material under conditions effective to reduce the amount of impurity compound in the first feed and produce (Continued)

a purified first feed. The purified first feed and at least part of the second feed are then contacted with an alkylation catalyst composition under alkylation conditions effective to convert at least part of the alkylatable aromatic compound in the purified first feed to the desired alkylaromatic compound and produce an alkylation effluent.

15 Claims, 3 Drawing Sheets

(51) Int. Cl.
  *B01J 8/02*     (2006.01)
  *B01J 20/22*    (2006.01)
  *C07C 7/12*     (2006.01)
  *C07C 7/13*     (2006.01)

(52) U.S. Cl.
  CPC .................. *C07C 7/12* (2013.01); *C07C 7/13* (2013.01); C07C 2529/08 (2013.01); C07C 2529/18 (2013.01); C07C 2529/40 (2013.01)

(56) References Cited

U.S. PATENT DOCUMENTS

| | | | |
|---|---|---|---|
| 3,415,736 A | 12/1968 | Ciric | 208/111 |
| 3,442,795 A | 5/1969 | Kerr et al. | 208/120 |
| 3,449,070 A | 6/1969 | McDaniel et al. | 23/111 |
| 3,702,886 A | 11/1972 | Argauer et al. | 423/328 |
| 3,709,979 A | 1/1973 | Chu | 423/328 |
| 3,766,093 A | 10/1973 | Chu | 252/455 |
| 3,832,449 A | 8/1974 | Rosinski et al. | 423/328 |
| RE28,341 E | 2/1975 | Wadlinger et al. | 208/120 |
| 3,894,104 A | 7/1975 | Chang et al. | 260/668 |
| 3,923,636 A | 12/1975 | Mead et al. | 208/58 |
| 3,950,496 A | 4/1976 | Ciric | 423/328 |
| 3,972,983 A | 8/1976 | Ciric | 423/328 |
| 4,016,218 A | 4/1977 | Haag et al. | 260/671 |
| 4,016,245 A | 4/1977 | Plank et al. | 423/328 |
| 4,021,947 A | 5/1977 | Shneider | 40/68.6 |
| 4,076,842 A | 2/1978 | Plank et al. | 423/328 |
| RE29,948 E | 3/1979 | Dwyer et al. | 208/110 |
| 4,234,231 A | 11/1980 | Yan | 299/4 |
| 4,401,556 A | 8/1983 | Bezman et al. | 208/111 |
| 4,439,409 A | 3/1984 | Puppe et al. | 423/328 |
| 4,556,477 A | 12/1985 | Dwyer | 208/111 |
| 4,826,667 A | 5/1989 | Zones et al. | 423/277 |
| 4,954,325 A | 9/1990 | Rubin et al. | 423/328 |
| 5,236,575 A | 8/1993 | Bennett et al. | 208/46 |
| 5,250,277 A | 10/1993 | Kresge et al. | 423/329.1 |
| 5,362,697 A | 11/1994 | Fung et al. | 502/71 |
| 6,077,498 A | 6/2000 | Diaz Cabanas et al. | 423/702 |
| 6,756,030 B1 | 6/2004 | Rohde et al. | 423/718 |
| 7,645,913 B2 | 1/2010 | Clark et al. | 585/449 |
| 7,713,513 B2 | 5/2010 | Jan et al. | 423/718 |
| 2013/0197287 A1 | 8/2013 | Vincent et al. | 585/320 |
| 2020/0179913 A1 | 6/2020 | Ide et al. | B01J 29/08 |

OTHER PUBLICATIONS

Lieb, A. et al. (2012) "MIL-100(V)—A Mesoporous Vanadium Metal Organic Framework with Accessible Metal Sites," *Micro. Meso. Mat.*, v.157, pp. 18-23.

PRODUCTION OF ALKYLAROMATIC COMPOUNDS

CROSS-REFERENCE TO RELATED APPLICATIONS

This application is a US national phase application of PCT Application Serial No. PCT/US2020/053510 having a filing date of Sep. 30, 2020, which claims priority to and the benefit of U.S. Provisional Application No. 62/926,174 having a filing date of Oct. 25, 2019 and European Patent Application No. 20158965.2 having a filing date of Feb. 24, 2020, the disclosures of all of which are incorporated herein by reference in their entireties.

FIELD

The present application relates to a process and system for producing alkylaromatic compounds, particularly ethylbenzene and cumene.

BACKGROUND

Ethylbenzene and cumene are valuable commodity chemicals which are used industrially for the production of styrene monomer and the coproduction of phenol and acetone, respectively. Ethylbenzene and cumene are typically produced by alkylating benzene with a $C_2$ or $C_3$ alkylating agent, such as ethylene or propylene, in the presence of an acid catalyst, particularly a zeolite catalyst.

Traditionally, ethylbenzene and cumene were produced in vapor-phase reactor systems but, at the high temperatures involved, side reactions can occur leading the production of by-products, such as xylenes and n-propylbenzene, which are difficult to remove from the desired ethylbenzene and cumene. More recently, the trend in the industry has been to shift away from vapor phase reactors to liquid phase reaction systems. Liquid phase aromatic alkylation plants run at relatively low temperatures and hence are less prone to produce undesirable by-products, such as xylenes. However, at these low temperatures, the acid catalysts involved can have great sensitivity to trace impurities or catalyst poisons in the feed streams, especially in the aromatic component of the feed. These poisons in the feed streams reduce the on-stream lifetime of the alkylation catalyst and can result in more frequent catalyst regeneration or replacement.

To address the issue of catalyst poisons, many current liquid phase aromatic alkylation processes employ a guard bed containing an adsorbent and located upstream of the alkylation catalyst. In some cases, the adsorbent is an acidic zeolite, normally a large pore zeolite, and a small stream of alkylating agent is added to the guard bed to react with the benzene feed. This is used as a marker for poison capacity. When the reactive sites of the adsorbent are no longer converting benzene to alkylated product, it is assumed that the adsorbent has met its poison capacity and needs to be regenerated. One such liquid phase alkylation process employing a reactive guard bed is disclosed in U.S. Pat. No. 7,645,913, in which the guard bed has more acid sites per unit volume of catalyst than the downstream alkylation catalyst There is, however, significant interest in developing improved guard bed adsorbents for liquid phase alkylation processes wherein the adsorbents exhibit increased capacity for feedstock poisons, particularly nitrogen- and oxygen-containing compounds, as compared with large pore zeolites.

SUMMARY

It has now been found that certain metal-organic framework (MOF) materials provide attractive adsorbents for removing poisons from aromatic alkylation feedstocks. While not normally exhibiting catalytic activity, MOFs can have a much larger adsorption capacity than large pore zeolites, such as zeolite beta and zeolite Y. Moreover, when the MOF material has reached is total sorption capacity, it can readily be regenerated and then returned to service.

This, in accordance with one aspect of the present application, there is provided a process for producing an alkylaromatic compound, the process comprising:

(a) providing a first feed comprising an alkylatable aromatic compound and a second feed comprising an alkylating agent, wherein at least the first feed contains an impurity compound comprising at least one of the following elements: nitrogen, halogens, oxygen, sulfur, arsenic, selenium, tellurium, phosphorus, and Group 1 through Group 12 metals;

(b) passing the first feed through an adsorbent comprising a metal-organic framework material under conditions effective to reduce the amount of impurity compound in the first feed and produce a purified first feed; and (c) contacting the purified first feed and at least part of the second feed with an alkylation catalyst composition under alkylation conditions effective to convert at least part of the alkylatable aromatic compound in the purified first feed to the desired alkylaromatic compound and produce an alkylation effluent.

In accordance with a further aspect of the present disclosure, there is provided a system for producing an alkylaromatic compound, the system comprising:

(a) a first bed comprising an adsorbent for contacting a first feed comprising an alkylatable aromatic compound containing an impurity compound comprising at least one of the following elements: nitrogen, halogens, oxygen, sulfur, arsenic, selenium, tellurium, phosphorus, and Group 1 through Group 12 metals under conditions effective to reduce the amount of impurity compound in the first feed and produce a purified first feed, wherein the adsorbent comprises a metal-organic framework material; and (b) a second bed downstream of, and connected to, the first bed for contacting the purified first feed with a second feed comprising an alkylating agent under alkylation conditions effective to convert at least part of the alkylatable aromatic compound in the purified first feed to the desired alkylaromatic compound and produce an alkylation effluent, wherein the second bed comprises an alkylation catalyst composition comprising a zeolite selected from the group consisting of beta, faujasite, mordenite and a zeolite of the MCM-22 family.

DETAILED DESCRIPTION OF THE EMBODIMENTS

Figure 1:
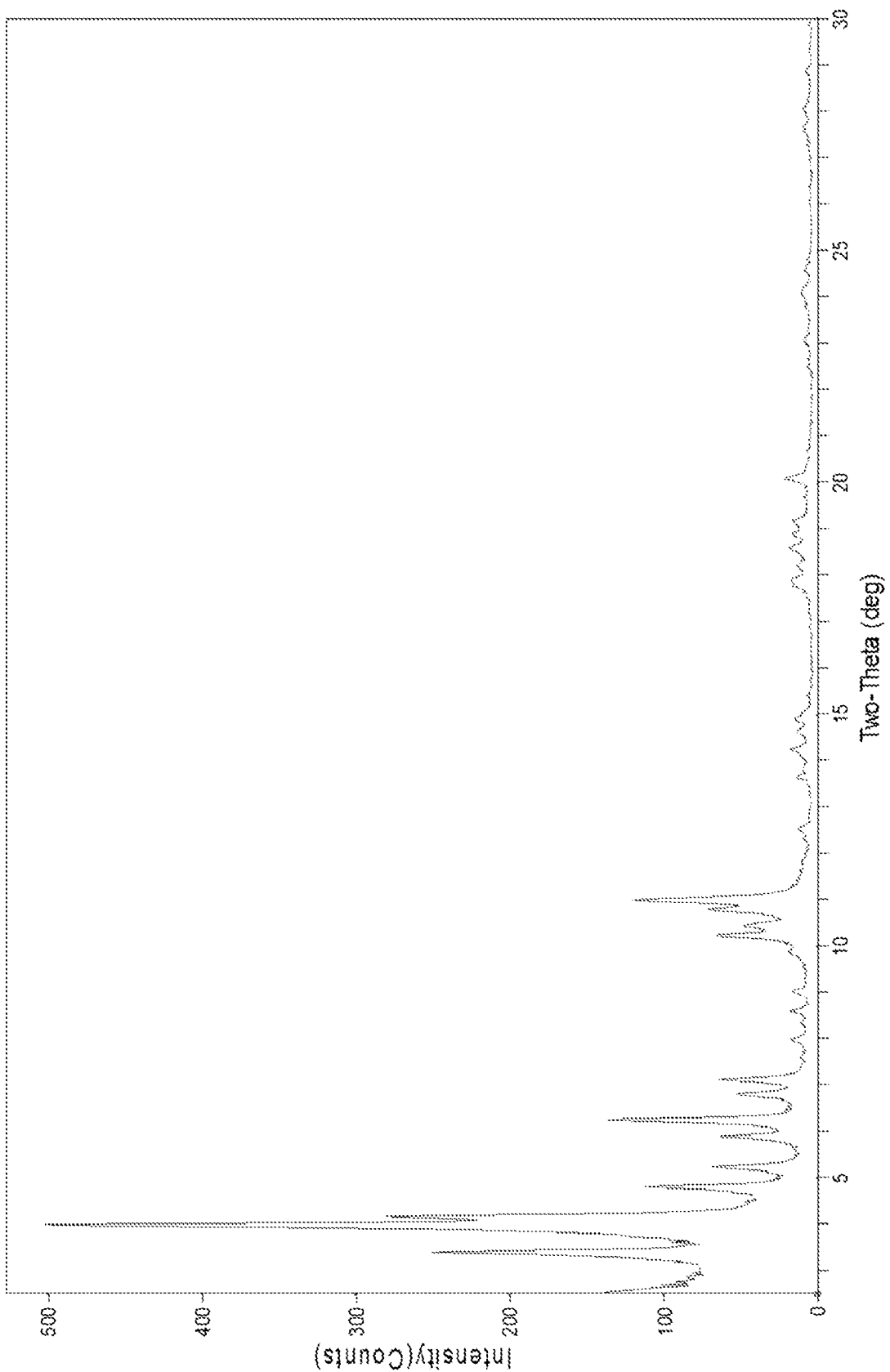
FIG. 1 is an X-ray diffraction pattern of the MIL-100 (Fe) material produced by the synthesis method of Example 1.

Described herein are a process and a system for producing an alkylaromatic compound, particularly ethylbenzene and/or cumene.

In one embodiment, there is provided a process for producing an alkylaromatic compound, in which a first feed comprising an alkylatable aromatic compound is reacted with a second feed comprising an alkylating agent in the presence of an alkylation catalyst composition. At least the first feed contains an impurity compound comprising at least one of the following elements: nitrogen, halogens, oxygen, sulfur, arsenic, selenium, tellurium, phosphorus, and Group 1 through Group 12 metals, or other material capable of poisoning the an alkylation catalyst composition. The first feed is passed through an adsorbent comprising a metal-organic framework material under conditions effective to reduce the amount of impurity compound in the first feed and produce a purified first feed, which is then contacted with at least part of the second feed in the presence of alkylation catalyst composition under alkylation conditions effective to convert at least part of the alkylatable aromatic compound in the purified first feed to the desired alkylaromatic compound and produce an alkylation effluent.

In some embodiments, the second feed also contains an impurity compound comprising at least one of the following elements: nitrogen, halogens, oxygen, sulfur, arsenic, selenium, tellurium, phosphorus, and Group 1 through Group 12 metals, or other material capable of poisoning the an alkylation catalyst composition. In this case, the process may further comprise passing the second feed through an adsorbent comprising a metal-organic framework under conditions effective to reduce the amount of impurity compound in the second feed and produce a purified second feed; and then reacting the purified second feed with the purified first feed. The adsorbent used to purify the second feed may be the same or different from the adsorbent used to purify the first feed and the first and second feeds may be passed through their respective adsorbent(s) simultaneously or at different times. A single bed of one of more metal-organic framework materials may be used to purify both the first and second feeds.

In a further embodiment, the present application provides system for producing an alkylaromatic compound, in which the system comprises a first bed comprising an adsorbent for contacting a first feed comprising an alkylatable aromatic compound containing an impurity compound comprising at least one of the following elements: nitrogen, halogens, oxygen, sulfur, arsenic, selenium, tellurium, phosphorus, and Group 1 through Group 12 metals under conditions effective to reduce the amount of impurity compound in the first feed and produce a purified first feed, wherein the adsorbent comprises a metal-organic framework material. In addition, the system comprises a second bed downstream of, and connected to, the first bed for contacting the purified first feed with a second feed comprising an alkylating agent under alkylation conditions effective to convert at least part of the alkylatable aromatic compound in the purified first feed to the desired alkylaromatic compound and produce an alkylation effluent Preferably, the second bed comprises an alkylation catalyst composition comprising a zeolite selected from the group consisting of beta, faujasite, mordenite and a zeolite of the MCM-22 family. The first and second beds may be contained in a single reactor or in separate reactors.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act completely deactivate the catalyst by poisoning the catalyst under the reaction conditions selected.

Substituted aromatic compounds which may be alkylated herein must possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which may be present as substituents on the aromatic compound contain from about 1 to 22 carbon atoms and usually from about 1 to 8 carbon atoms, and most usually from about 1 to 4 carbon atoms. Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate or cut thereof containing substantial quantities of benzene (>1%), toluene and/or xylene constitutes a particularly useful feed for the alkylation process of this disclosure.

As used herein, the term "alkylating agent" includes any compound capable of reaction with an alkylatable aromatic compound to produce an alkylaromatic product. Suitable alkylating agents include alkenes, alcohols and alkyl halides. Preferred alkylating agents comprise alkenes, such as ethylene, propylene, 1-butene and 2-butene, preferably ethylene.

Preferably, the reactants in the process of the disclosure are benzene and ethylene or propylene and the desired reaction product is ethylbenzene or cumene.

In embodiments, the alkylatable aromatic material, and in some cases the alkylating agent, contains at least one impurity compound, such as is typically found in commercially available feedstocks. Examples of such impurity compounds comprise at least one of the following elements: nitrogen, halogens, oxygen, sulfur, arsenic, selenium, tellurium, phosphorus, and Group 1 through Group 12 metals, or other material capable of poisoning the an alkylation catalyst composition. Specific impurity compounds include, for example, nitrogen-containing, sulfur-containing, and oxygen-containing compounds, especially basic nitrogen-containing compounds. Such compounds may be present in amounts of less than 20 ppm, less than 15 ppm, less than 10 ppm, less than 5 ppm or less than 1 ppm by weight.

In the present process, the first feed comprising the alkylatable aromatic compound together with at least one impurity is initially passed through an adsorbent comprising a metal-organic framework material or MOF. As used herein, the term "metal-organic framework" or "MOF" refers to a class of porous materials that are comprised of metal ion/oxide secondary building units (SBUs) interconnected by organic linking ligands. MOFs are characterized by low densities, high internal surface areas, and uniformly sized pores and channels. Whereas virtually any MOF can be used as the adsorbent in the present process, the preferred MOF materials for use herein have an internal surface area of at least 1000 m$^2$/g, especially at least 1500 m$^2$/g. Examples of suitable MOF materials include those in which the organic linking ligand comprises a carboxylate group, particularly a benzenecarboxylate group. In some embodiments, the MOF material has the MIL-100 structure, the structure and synthesis of which are described in, for example, Chemical Communications, 2007, 2820-2822 Specific MOF materials of use herein include MIL-100 (M) materials where M=Cr, Fe, Sc, Al, and/or V, especially Fe, Cr and/or V. MIL-100 (Fe) is particularly preferred. This is believed to be, without any specific description of the mechanism, to be the result of open metal sites decorating the internal pore of the material. With this assumption, MOF materials that comprise open metal sites such as HKUST-1, CPO-27/MOF-74, MIL-101, and MIL-88 are expected to be effective for this application in some capacity.

The conditions employed in the adsorption process are generally not critical but typically include a temperature from about 30 to 200° C., and preferably between about 60 to 150° C., a weight hourly space velocity (WHSV) of from about 0.1 hr$^{-1}$ and about 200 hr$^{-1}$, preferably from about 0.5 hr$^{-1}$ to about 100 hr$^{-1}$, and more preferably from about 1.0 hr$^{-1}$ to about 50 hr$^{-1}$; and a pressure from ambient to about 3000 kPa-a.

Passing the first feed comprising the alkylatable aromatic compound through the MOF adsorbent under these conditions reduces the amount of impurity compound in the first feed by at least about 25%, and produces a purified first feed, which typically contains less of the impurity compound. When the MOF has reached its capacity for adsorbing the impurity compound, the spent MOF can be readily regenerated using a hot stripping gas or by a displacement desorption process in which steam or some other binding gas is used to displace the impurity-containing molecules from the MOF adsorbent. The regenerated MOF can then be returned to sorption service.

After passage through the adsorbent described above, the purified first feed is contacted with the second feed, either with or without prior purification of the second feed, in the presence of an alkylation catalyst composition under alkylation conditions effective to convert at least part of the alkylatable aromatic compound in the purified first feed to the desired alkylaromatic compound and produce an alkylation effluent.

In some embodiments, the alkylation catalyst composition employed in the present process comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In other embodiments, the alkylation catalyst composition employed in the present process comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Patent No. MCM-56 (described in U.S. Pat. No. 5,362,697), UZM-8 (described in U.S. Pat. No. 6,756,030), UZM-8HS (described in U.S. Pat. No. 7,713,513) and mixtures thereof.

In further embodiments, the alkylation catalyst composition employed in the present process comprises one or more large pore molecular sieves having a Constraint Index less than 2. Suitable large pore molecular sieves include zeolite beta, zeolite Y, Ultrastable Y (USY), Ultrahydrophobic Y (UHP-Y), Dealuminized Y (Deal Y), mordenite, ZSM-3, ZSM-4, ZSM-14, ZSM-18, ZSM-20 and mixtures thereof. Zeolite ZSM-3 is described in U.S. Pat. No. 3,415,736. Zeolite ZSM-4 is described in U.S. Pat. No. 4,021,947. Zeolite ZSM-14 is described in U.S. Pat. No. 3,923,636.

Zeolite ZSM-18 is described in U.S. Pat. No. 3,950,496. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferred molecular sieves for the alkylation reaction comprise zeolite beta, molecular sieves having a Constraint Index of 2-12, especially ZSM-5, faujasite, mordenite and molecular sieves of the MCM-22 family.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation reaction can be conducted in any suitable reactor such as a fixed bed reactor, a moving bed reactor, a fluidized bed reactor and a reaction distillation unit. A fixed bed reactor is generally preferred. In addition, although a single alkylation reactor can be employed, in some embodiments multiple reactors connected in series can be used with each reactor containing one or more of the catalysts described above.

The alkylation reaction in the or each alkylation reactor may takes place under at least partly liquid conditions, such that the alkylatable aromatic compound is either completely in the liquid phase or partly in the vapor phase and partly in the liquid phase. In this respect, it is to be appreciated that maintaining the alkylatable aromatic compound in the liquid phase or the ratio of the volume of liquid to the volume of vapor in a mixed phase alkylation reactor is a function of many variables, including temperature, pressure, alkene feed composition, the weight ratio of aromatics to alkene, and the number of interstage feed injection points (feed distribution among the reaction zones). Each of these variables must be understood and monitored in order to maintain the ratio of the volume of liquid to the volume of vapor at the desired level.

Particular conditions for carrying out the liquid or mixed phase alkylation of benzene with ethylene to produce ethylbenzene may include a temperature of from about 120 to about 270° C., a pressure of about 675 to about 8300 kPa, a WHSV based on ethylene of from about 0.1 to about 10 $hr^{-1}$, and a mole ratio of benzene to ethylene from about 1 to about 10.

Particular conditions for carrying out the liquid or mixed phase alkylation of benzene with propylene to produce cumene may include temperature of about 75 to about 250° C., a pressure of about 1000 kPa to about 5000 kPa, a WHSV based on propylene of from about 0.1 to about 10 $hr^{-1}$, and a mole ratio of benzene to propylene from about 1 to about 10.

Particular conditions for carrying out the liquid or mixed phase alkylation of benzene with 1-butene and/or 2-butene to produce sec-butylbenzene may include a temperature of about 75 to about 25 0° C., a pressure of about 500 kPa to about 4000 kPa, a WHSV based on butene of from about 0.1 to about 10 $hr^{-1}$ and a mole ratio of benzene to butene from about 1.0 to about 5.0.

The invention will now be more particularly described with reference to the following non-limiting Examples and the accompanying drawings.

Example 1: Synthesis of MIL-100 (Fe)

MIL-100 (Fe) was produced in a method analogous to that represented in Chemical Communications 27, 2007, 2820-2822.

Iron (III) nitrate nonahydrate (20.2 g) and 1,3,5-benzenetricarboxylic acid (5.67 g) were suspended in 30 mL of deionized water in a 100 mL round bottomed flask. A magnetic stir bead was added and the mixture was heated overnight at 95° C. with magnetic stirring for 18 hours. Following the reaction, the slurry was filtered and washed with a 50/50 mixture of ethanol and water. To purify, the material was suspended in 200 mL of ethanol. 300 mg of $NH_4F$ (dissolved in minimal water) was then added to this suspension and the mixture stirred at 70° C. for 3-5 hours. The MIL-100 was then filtered and washed with ethanol via soxhlet extraction for 16 hours. The material was dried at 90° C. under air resulting in dry MIL-100 powder. The X-ray diffraction pattern of the resultant material is shown FIG. 1.

Figure 2:
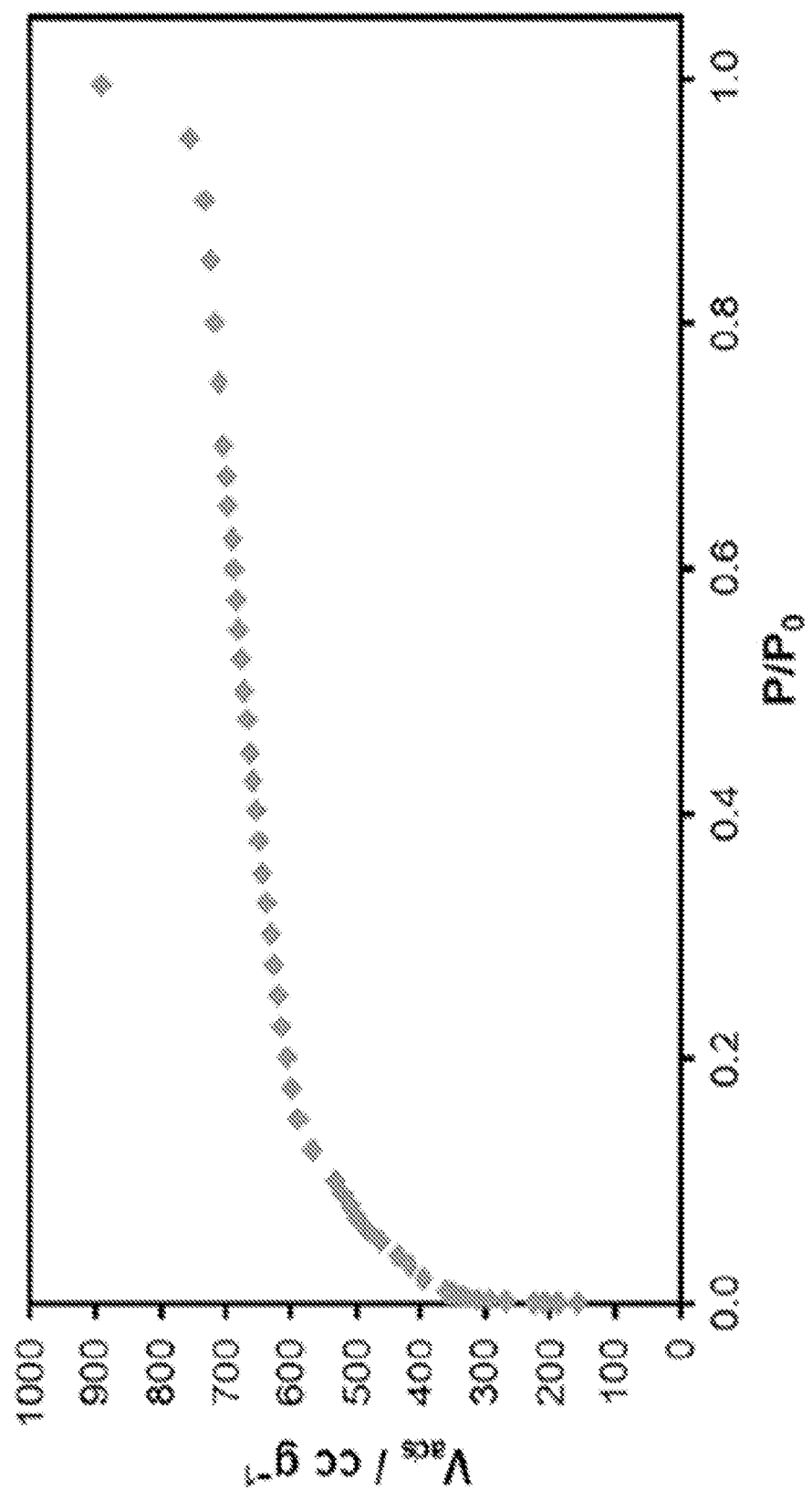
FIG. 2 is the nitrogen adsorption isotherm at 77° K for the MIL-100 (Fe) material produced by the synthesis method of Example 1 after activation at 180° C. for 18 hours.

FIG. 2. Nitrogen adsorption on MIL-100 (Fe) sample synthesized by the above method after activation at 180° C. under vacuum for 18 hours is shown in FIG. 2. As measured using the BET method, the apparent surface area of the MIL-100 (Fe) sample was approximately 2240 m2/g with a micropore surface area of 1980 $m^2/g$. The pore volume for this sample is 0.910 cc/g.

Example 2: Synthesis of MIL-100 (V)

MIL-100 (V) was synthesized by a method analogous to that represented in Microporous Mesoporous Materials 157, 2012, 18-23.

628 mg of $VCl_3$ and 588 mg of trimethylbenzenetribenzoate were put into 5 mL of water and heated to 220° C. for 72 hours. The material was then cooled and then washed with water and ethanol to yield MIL-100 (V).

Example 3: Synthesis of MIL-100 (Cr)

MIL-100 (Cr) was synthesized from an adaptation of the MIL-100 (V) synthesis described in Example 2 in which Cr was substituted for vanadium.

1.08 grams of chromium trichloride hexahydrate and 588 mg of trimethyl-1,3,5-benzenetricarboxylate and 0.1519 grams of ammonium fluoride were added to 5 mL of water. The reaction was heated to 220° C. for 72 hours then cooled, filtered, and washed with water and ethanol to yield MIL-100 (Cr).

Example 4: Adsorption Testing

A static nitrogen adsorption test was used to evaluate the ability of the MOF materials of Examples 1 to 3 to remove N-formylmorpholine (NFM) from an aromatic hydrocarbon feed. For comparison, the test was also conducted on a commercially available large pore zeolite sample. In the tests, ethylbenzene (EB). was used as a surrogate to benzene. EB was used as a surrogate given the hazards of using benzene and was spiked to 20 ppm NFM (as measured by nitrogen content). Each adsorbent was added to a separate sample of the EB/NFM solution at a loading of 5 mg/g solution for a fixed period of times of 5 minutes and minutes at ambient conditions (~23° C.).

Figure 3:
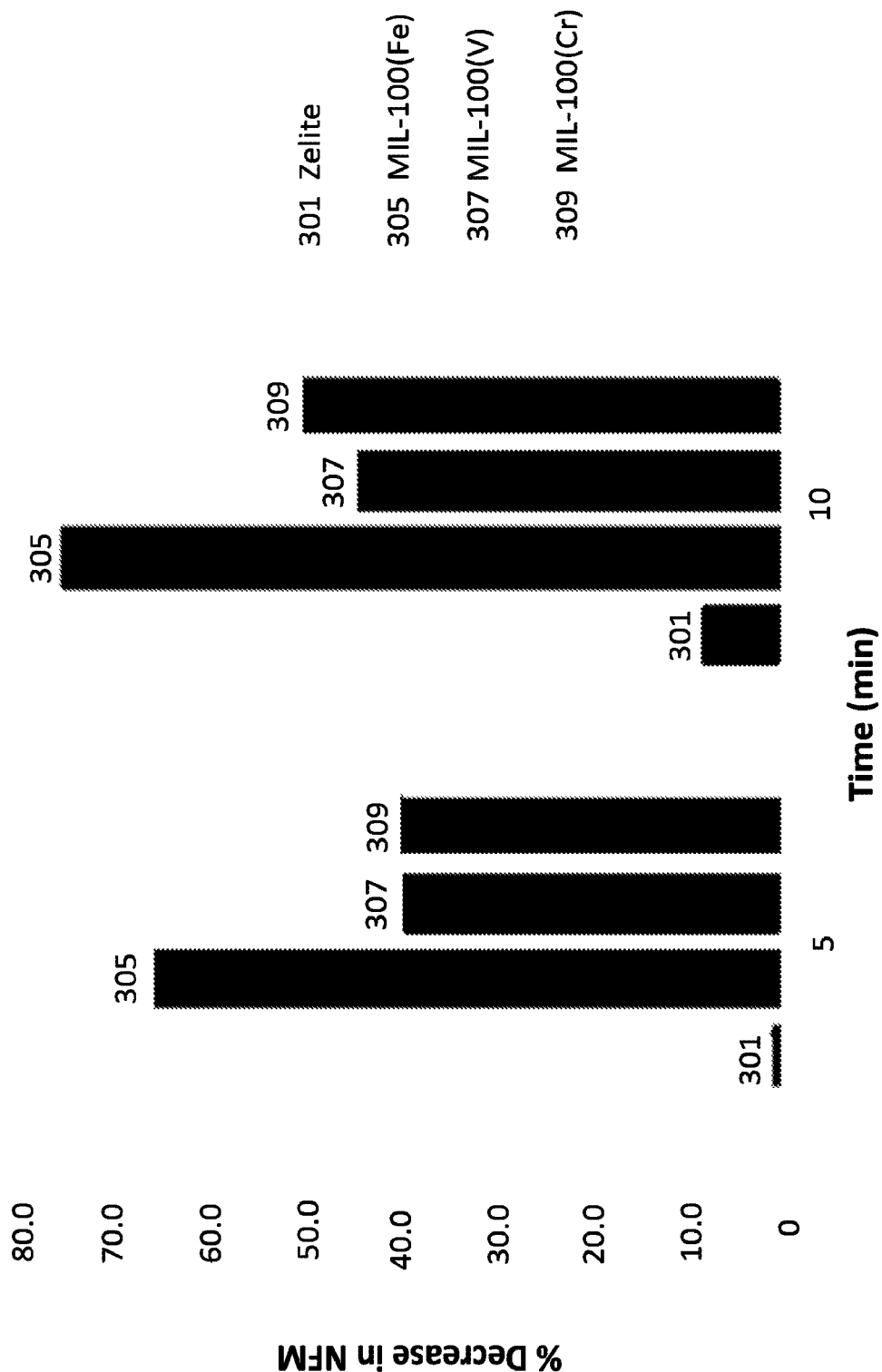
FIG. 3 is a graph comparing the N-formylmorpholine (NFM) adsorption capacity of the MIL-100 (Fe) material of Example 1 with the MIL-100 (V) material of Example 2, the MIL-100 (Cr) material of Example 3 and a large pore zeolite material.

Chemiluminescence was used to analyze the N content of the solution before and after adsorption. As shown in FIG. 3, the MOF materials (Examples 2, 3, and 4, shown as materials 305, 307, 309 respectively) removed significantly more NFM than the zeolite standard (material 301).

The invention claimed is:

1. A process for producing an alkylaromatic compound, the process comprising:
   (a) providing a first feed comprising an alkylatable aromatic compound and a second feed comprising an alkylating agent, wherein at least the first feed contains an impurity compound comprising at least one of the following elements: nitrogen, halogens, oxygen, sulfur, arsenic, selenium, tellurium, phosphorus, and Group 1 through Group 12 metals;
   (b) passing the first feed through an adsorbent comprising a metal-organic framework material under conditions effective to reduce an amount of impurity compound in the first feed and produce a purified first feed; and
   (c) contacting the purified first feed and at least part of the second feed with an alkylation catalyst composition under alkylation conditions effective to convert at least part of the alkylatable aromatic compound in the purified first feed to the alkylaromatic compound and produce an alkylation effluent.

2. The process of claim 1, wherein the second feed also contains an impurity compound comprising at least one of the following elements: nitrogen, halogens, oxygen, sulfur, arsenic, selenium, tellurium, phosphorus, and Group 1 through Group 12 metals and the process further comprises:
   (d) passing the second feed through an adsorbent comprising a metal-organic framework under conditions effective to reduce an amount of impurity compound in the second feed and produce a purified second feed; and
   (e) supplying the purified second feed to the contacting (c).

3. The process of claim 2, wherein the adsorbent that the first feed passes through and the adsorbent that the second feed passes through is the same.

4. The process of claim 2, wherein the adsorbent that the first feed passes through and the adsorbent that the second feed passes through is the same, and the first feed and the second feed are passed simultaneously through the adsorbent.

5. The process of claim 1, wherein the alkylatable aromatic compound comprises benzene.

6. The process of claim 1, wherein the alkylating agent comprises ethylene.

7. The process of claim 1, wherein the alkylating agent comprises propylene and/or isopropanol.

8. The process of claim 1, wherein the impurity compound contains nitrogen and/or oxygen.

9. The process of claim 1, wherein the metal-organic framework material has a MIL-100 structure.

10. The process of claim 9, wherein the metal of the metal-organic framework material comprises iron, vanadium and/or chromium.

11. The process of claim 1, wherein the alkylatable aromatic compound is at least partly in a liquid phase in the contacting (c).

12. The process of claim 1, wherein the alkylation catalyst composition comprises a zeolite selected from the group consisting of ZSM-5, beta, faujasite, mordenite and a zeolite of the MCM-22 family.

13. A system for producing an alkylaromatic compound, the catalyst system comprising:
   (a) a first bed comprising an adsorbent for contacting a first feed comprising an alkylatable aromatic compound containing an impurity compound comprising at least one of the following elements: nitrogen, halogens, oxygen, sulfur, arsenic, selenium, tellurium, phosphorus, and Group 1 through Group 12 metals under conditions effective to reduce an amount of impurity compound in the first feed and produce a purified first feed, wherein the adsorbent comprises a metal-organic framework material; and
   (b) a second bed downstream of, and connected to, the first bed for contacting the purified first feed with a second feed comprising an alkylating agent under alkylation conditions effective to convert at least part of the alkylatable aromatic compound in the purified first feed to the alkylaromatic compound and produce an alkylation effluent, wherein the second bed comprises an alkylation catalyst composition comprising a zeolite selected from the group consisting of beta, faujasite, mordenite and a zeolite of the MCM-22 family.

14. The catalyst system of claim 13, wherein the metal-organic framework material has MIL-100 structure.

15. The catalyst system of claim 14, wherein the metal of the metal-organic framework material comprises iron, vanadium and/or chromium.

* * * * *